(12) United States Patent
Elder et al.

(10) Patent No.: US 6,639,106 B1
(45) Date of Patent: Oct. 28, 2003

(54) PROCESS FOR PREPARING AND PURIFYING ACRYLIC ACID FROM PROPYLENE HAVING IMPROVED CAPACITY

(75) Inventors: James Edward Elder, Houston, TX (US); Charles Michael Lonzetta, Houston, TX (US); Peter David Klugherz, Huntingdon Valley, PA (US); Donald Alan Ebert, Houston, TX (US); Elaina Lashae Williams, Blakeslee, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/619,403

(22) Filed: Jul. 19, 2000

Related U.S. Application Data

(60) Provisional application No. 60/145,308, filed on Jul. 23, 1999.

(51) Int. Cl.$^7$ .......................... C07C 51/42; C07C 51/16
(52) U.S. Cl. ........................................ 562/600; 562/532
(58) Field of Search ................................. 562/532, 600

(56) References Cited

U.S. PATENT DOCUMENTS

| | | |
|---|---|---|
| 3,775,474 A | 11/1973 | Ohara et al. |
| 3,893,951 A | 7/1975 | Grasselli et al. |
| 3,954,855 A | 5/1976 | Wada et al. |
| 4,075,127 A | 2/1978 | Kadowaki et al. |
| 4,203,906 A | 5/1980 | Takada et al. |
| 4,256,783 A | 3/1981 | Takada et al. |
| 4,365,087 A | 12/1982 | Kadowaki et al. |
| 4,873,368 A | 10/1989 | Kadowaki et al. |
| 5,144,091 A | 9/1992 | Martan et al. |
| 5,177,260 A | 1/1993 | Kawajiri et al. |
| 5,198,578 A | 3/1993 | Etzkorn et al. |
| 5,264,625 A | 11/1993 | Hammon et al. |
| 5,446,004 A | 8/1995 | Tenten et al. |
| 5,493,052 A | 2/1996 | Tenten et al. |
| 5,739,391 A | 4/1998 | Ruppel et al. |
| 5,739,392 A | 4/1998 | Tanimoto et al. |

FOREIGN PATENT DOCUMENTS

| | | |
|---|---|---|
| DE | 2201528 | 11/1972 |
| EP | 0293 224 | 11/1988 |
| EP | 0695 736 A1 | 2/1996 |
| WO | WO 97/36849 | 10/1997 |

*Primary Examiner*—Paul J. Killos

(57) ABSTRACT

This invention relates to an improved process for preparing acrylic acid from propylene using a tandem reactor and utilizing an increased amount of propylene reactant, thereby providing increased capacity and throughput. An improved process for purifying acrylic acid is also disclosed.

11 Claims, 1 Drawing Sheet

PROCESS FOR PREPARING AND PURIFYING ACRYLIC ACID FROM PROPYLENE HAVING IMPROVED CAPACITY

This application claims the benefit of provisional application Ser. No. 60/145,308 field Jul. 23, 1999.

This invention relates to an improved process for preparing acrylic acid from propylene using first and second stage reactors, "tandem reactors" and an improved process for purifying the acrylic acid. In particular, the invention relates to a tandem reactor process for preparing acrylic acid from propylene utilizing an increased concentration of propylene reactant thereby providing increased capacity and throughput.

The preparation of acrylic acid from propylene generally proceeds in a vapor phase two stage catalytic oxidation reaction. In the first stage propylene is oxidized in the presence of oxygen, diluent inert gasses, water vapor, and appropriate catalysts to produce acrolein according to equation (I):

$$C_3H_6 + O_2 \rightarrow C_2H_3CHO + H_2O + \text{heat} \tag{I}$$

The acrolein is then oxidized, in a second stage, in the presence of oxygen, diluent inert gasses, water vapor, and appropriate catalysts to form acrylic acid according to equation (II):

$$C_2H_3CHO + \tfrac{1}{2}O_2 \rightarrow C_2H_3COOH + \text{heat} \tag{II}$$

The two stage vapor phase catalytic oxidation of propylene to acrylic acid is generally performed using either tandem reactors wherein a separate reactor is utilized for each step, e.g., see the description in U.S. Pat. No. 4,873,368, or by utilizing one reactor to perform both steps, e.g., see the description in U.S. Pat. No. 4,526,783.

The acrylic acid prepared using such a vapor phase catalytic oxidation reaction is present in a mixed product gas exiting the second stage reactor. Generally, the mixed product gas is cooled and is contacted with an aqueous stream in an absorption tower, thereby providing an aqueous acrylic acid solution from which acrylic acid can be isolated and purified. The remainder of the product gasses, known as the absorber waste gas or absorber off-gas, is incinerated. Depending on the reactants feed gas composition, the absorber off-gas may contain inert gasses, $O_2$, water vapor, CO, $CO_2$, unreacted propylene, unreacted acrolein and/or acrylic acid.

The tandem reactor processes known in the art are useful, however there is a continuing need for a process which is more efficient. By more efficient is meant a process which provides more acrylic acid with the same or smaller equipment, or creates less waste. Generally, increasing the propylene was thought in the art to be an unsuitable mechanism for increasing throughput and efficiency in the process because of the dangers of flammability and run-away reactions. Consequently, the oxidation of propylene to acrylic acid is generally practiced in the art utilizing a propylene concentration in the reactant gas feed composition of between 4 and 7 volume percent of the total reactant feed composition (see for example col. 2, lines 42–46 of U.S. Pat. No. 4,873,368).

U.S. Pat. Nos. 4,365,087 and 4,873,368 have dealt with the problem of increasing process productivity/capacity by raising the propylene concentration level. The processes disclosed in these references used a tandem reactor process whereby either the temperature of the feed was limited (<260° C.), the oxygen to propylene molar ratio (1.1–2.0:1, preferably lower than 1.8) was kept low, additional oxygen and inert gas was fed to the second stage reactor, and the reaction was quenched somewhat before introduction to the second stage ('087) or the oxygen to propylene molar ratio (1.17–1.66:1) was even lower, additional oxygen and inert gas was fed to the second stage reactor, and the reaction was quenched somewhat before introduction to the second stage. The quenching was achieved through passing the products of the first stage reaction through a bed of a solid inactive material. Passing the products through this bed results in a pressure drop. The technique relied on two mechanisms for controlling the reaction at higher propylene concentrations:

(1) tightly controlling the temperature before entry into the first stage reactor and/or the second stage reactor; and (2) limiting the amount of oxygen initially available to the first reactor for oxidation of propylene to acrolein and then adding more oxygen and diluent at the interstage before the second stage reactor so that the second reactor feed has a stoichiometrically sufficient amount of oxygen to allow suitable oxidation of acrolein to acrylic acid.

It generally is undesirable to require feeding additional oxygen to the second stage of the reaction because of, as with the first stage, the possibility of increased incidence of flammability problems and runaway reactions. It is also undesirable to have a pressure drop due to cooling through a solid bed because resultant pressure drops lead to reduced selectivity for acrolein or acrylic acid.

The present inventors have now discovered that with the tandem reactor system described herein it is possible to provide feeds to the reactors which contain a high concentration of propylene without the problems associated with the cited processes. Such high concentration feeds are accomplished without the need to utilize a lower oxygen-:propylene feed ratio, and the consequent addition of oxygen and inert gas to the second stage to assure proper stoichiometry. Applicants have also avoided the pressure drop associated with cooling through a solid bed, by substituting a heat exchanger for cooling purposes.

Accordingly, a novel process for preparing acrylic acid from propylene is described herein wherein the following advantages are provided:

(1) downstream debottlenecking is realized through producing an aqueous acrylic acid stream in the absorber having a higher concentration of acrylic acid because less water is present;

(2) since there is less water condensed in the aqueous acrylic acid there is a reduction in the waste generated by the process; and (3) there is a lower pressure drop in the reactors, due to increased feed composition, which offsets increased propylene partial pressure, thereby preventing lower acrylic acid selectivity resulting from higher propylene pressure.

In one aspect of the present invention, there is provided a process for the vapor phase oxidation of propylene to acrylic acid, comprising the steps of: (A) feeding a reactant composition comprising: (i) greater than 7 percent by volume propylene, (ii) oxygen, (iii) water vapor, and (iv) the remainder including a major amount of at least one inert gas, into a reactor; the reactor including a plurality of contact tubes, containing at least one catalyst, disposed in a shell, wherein the inside of the reactor shell contains at least one heat transfer zone through which a heat transfer medium passes and each contact tube comprises at least one reaction zone capable of effecting the preparation of acrolein from propylene, (B) contacting the reactant composition with the at least one reaction zone to form a mixed product gas comprising acrolein, (C) cooling the mixed product gas comprising acrolein in a heat exchanger, (D) feeding the mixed product gas comprising acrolein to a second reactor; the second reactor including a plurality of contact tubes, containing at least one catalyst, disposed in a shell, wherein the inside of the reactor shell contains at least one heat transfer zone through which a heat transfer medium passes and each contact tube comprises at least one reaction zone capable of effecting the preparation of acrylic acid from acrolein, and (E) contacting the reactant composition with the at least one reaction zone to form a mixed product gas comprising acrylic acid.

BRIEF DESCRIPTION OF THE FIGURE

The process of the present invention will be described herein with reference to FIG. 1.

The oxidation process is described according to FIG. 1 as follows: air, steam, and propylene are fed into reactor 1 and reacted to form a mixed product gas containing acrolein. The mixed product gas containing acrolein is then fed to the heat exchanger 2 and cooled. The cooled mixed product gas containing acrolein is then fed to reactor 3 and reacted to form a mixed product gas containing acrylic acid. The mixed product gas containing acrylic acid is then fed to absorber 4, where it is contacted with water to form an aqueous acrylic acid stream.

Figure 1:
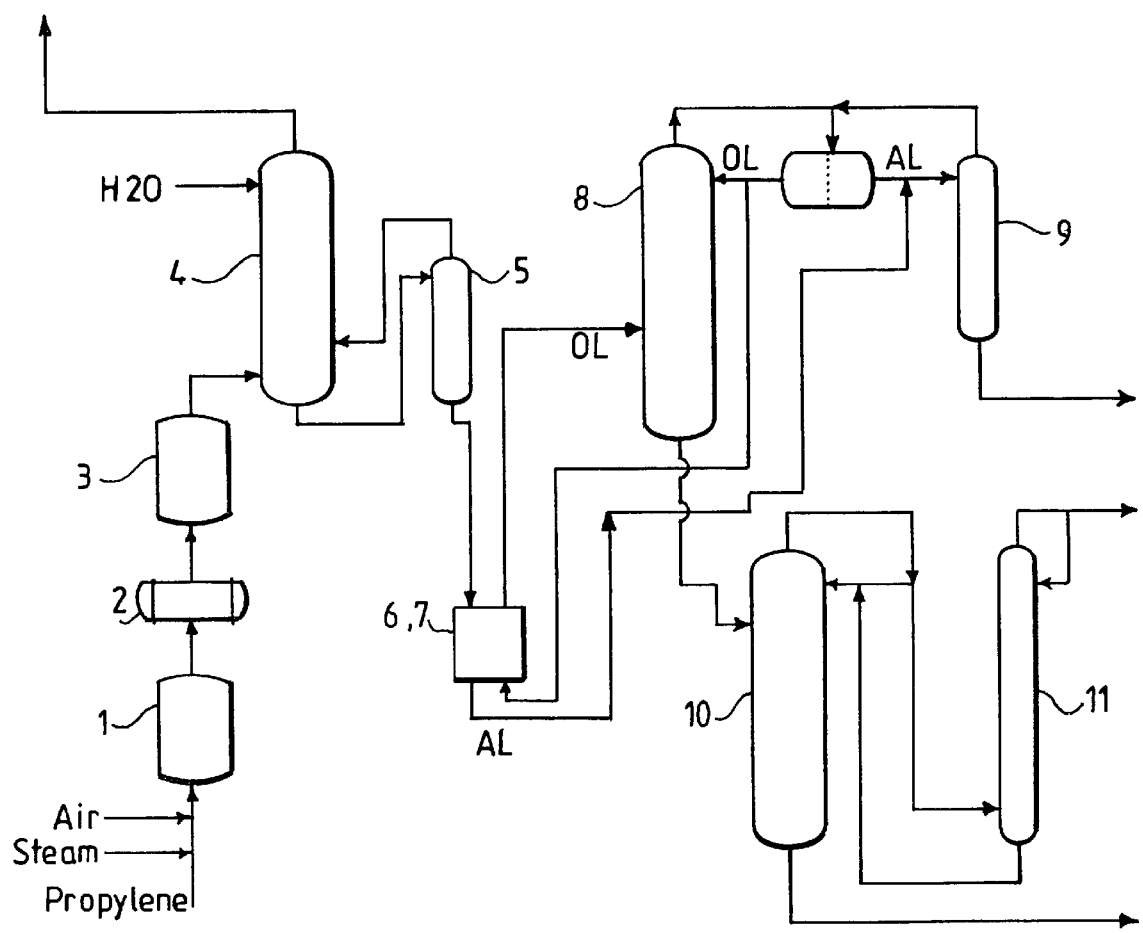

The propylene used may be from any source and may be any grade suitable for an acrylic acid producing vapor phase oxidation reaction. Suitable grades include, but are not limited to, polymer grade (generally greater than or equal to 99% propylene by volume), chemical grade (generally greater than or equal to 94% propylene by volume), and refinery grade (generally greater than or equal to 60% propylene by volume). In a preferred embodiment, the propylene is chemical grade propylene. Use of chemical grade propylene has the added advantage of providing combustible materials such as propane which are present as impurities. The propane provides more inert gas to the system, but more importantly provides fuel for the thermal/catalytic oxidation or incineration of that portion of the absorber off-gas which is not recycled. Accordingly, the propane impurity enters the thermal/catalytic oxidizer or incinerator with the absorber off-gas and reduces the additional fuel required to burn the off-gas. Generally, chemical grade propylene contains up to 6 percent combustible impurities and refinery grade propylene contains up to 40 percent combustible impurities.

Propylene is generally present in the reactant composition at greater than 7 percent by volume of the reactant composition. In one embodiment, propylene is present at a range of from 7.01 to 11, preferably, 7.01 to 9, more preferably 7.5 to 9 percent by volume of the reactant composition.

The oxygen in the reaction composition may be provided by any material containing an amount of oxygen sufficient to maintain the oxidation reactions in equations (I) and (II) above. Suitable examples include, without limitation, air, oxygen-enriched air, pure oxygen, and mixtures of pure oxygen and at least one inert gas or mixtures thereof. The preferred source of oxygen is air. Typically oxygen is present in the reactant composition in an amount suitable to meet the stoichiometric needs of the reaction. Generally, an amount of oxygen which will provide an oxygen/propylene ratio in the reactant composition of 1.6 to 2.2:1.0, preferably 1.6 to 2.0:1.0, is provided.

The water vapor in the reaction composition is generally present at a range from 10 to 40 percent by volume, preferably 15 to 25 percent by volume of the reactant composition.

The inert gas used in the reaction composition may be any gaseous material or mixtures of gaseous materials which is inert to the oxidation reactions depicted in equations (I) and (II) above. Typical examples include, but are not limited to, nitrogen, carbon dioxide, helium, argon, propane and carbon monoxide, or mixtures thereof. The preferred inert gas is nitrogen or a mixture of nitrogen with at least one other inert gas. The inert gas generally constitutes a major amount of the remainder of the reactant composition which is not propylene, oxygen, or water vapor. Generally, the inert gas is 50 to 99.9, preferably 60 to 99.9 volume percent of the remainder of the reactant composition.

As recited above, the reaction composition may optionally include at least one inert gas which is suitable for use as fuel for thermal oxidation/incineration of waste absorber off-gas. Such inert gas fuel may be provided as part of the impurities in the propylene feed, as part of the absorber off-gas, or as the neat chemical. Suitable examples include, but are not limited to, propane, ethane, methane, butane, pentane or mixtures of one or more of the above. The preferred inert gas fuel is propane. Generally, such inert gas fuel is present in a minor amount in the remainder of the reactant composition which does not include propylene, oxygen and water vapor. Generally, the inert gas fuel is 0.001 to 49.9, preferably 0.1 to 20 volume percent of the total reactant feed composition.

The reactors 1 and 3 are shell and multiple contact tube heat exchange reactors. The contact tubes utilized are those generally known and used in the art. The contact tubes may be arranged in any suitable arrangement known in the art. Such suitable arrangements are described and disclosed in, for instance, U.S. Pat. Nos. 4,256,783; 5,151,605; and DE 2,201,528. The first layer in the top of the contact tube is a diluent material which is primarily ceramic balls or cylinders. Suitable ceramic materials as well as other type materials include, without limitation, one or more of the following: silicon dioxide, silicon carbide, silicon nitride, silicon boride, silicon boronitride, aluminum oxide (alumina), aluminosilicate (mullite), alundum, aluminoborosilicate, carborundum, carbonfiber, refractory fiber, zirconium oxide, yittrium oxide, calcium oxide, magnesium oxide, magnesium oxide-aluminosilicate (cordite), and clay based materials. Suitable diluent materials are available, for instance, from Norton Chemical Process Products Corp., of Akron, Ohio as the Denstone® line of catalyst supports.

As it passes the diluent material the reactant composition is preheated to near the temperature of the heat transfer medium before it enters the reaction zone. In the first stage reactor, the reaction zone contains at least one of a catalyst, a mixture of a catalyst capable of catalyzing the oxidation of propylene to acrolein and a diluent material, or a mixture of catalysts and a diluent material. In the second reactor, the reaction zone contains at least one of a catalyst, a mixture of a catalyst capable of catalyzing the oxidation of acrolein to acrylic acid and a diluent material, or a mixture of catalysts and a diluent material.

The mixture of catalyst and diluent material is less active than pure catalyst, thus making the reaction cooler and easier to control at the high initial propylene concentration. Determination of the amount of dilution of the catalyst is within the skill of those skilled in the art and generally is dependent on, for example, the particular catalyst utilized as well as the age of the catalyst and the operating conditions of the process. As the gas flows down the tube, the temperature increases as the reaction rate increases, then cools down as the propylene concentration decreases.

Any catalysts suitable for the vapor phase catalytic oxidation of propylene to acrolein and acrolein to acrylic acid may be used in the process of the present invention. Such catalysts are known in the art and are described in, for instance U.S. Pat. Nos. 3,775,474; 3,893,951; 3,954,855; 4,075,127; 4,365,087; 4,873,368; 5,144,091; 5,177,260; 5,198,578; 5,264,625; 5,739,391; 5,739,392; WIPO Patent App. No. WO 97/36849; and Canadian Patent App. No. 2,114,681.

Each heat transfer zone of each reactor has circulating within it a heat transfer medium which is used to maintain an effective catalyst temperature profile and therefore reaction temperature. Maintaining a desired catalyst temperature profile is required for maintaining the optimum acrylic acid yield and for optimizing catalyst life. If the reaction temperature is too high, more carbon dioxide and carbon monoxide are formed thereby resulting in lower yields. Furthermore, the catalyst will age quicker under excessive reaction temperatures. Of course, if the temperature gets high enough an uncontrolled runaway reaction may occur. If not controlled, such a reaction could lead to catalyst destruction and/or explosive conditions. If the reaction temperature is too low, less propylene will be converted to acrolein and acrolein to acrylic acid so that yields will be lower. If the reaction temperature is excessively low, propylene and/or acrolein may travel downstream leading to serious consequences, such as a fire or explosion.

The heat transfer medium circulates within each reactor heat transfer zone thereby transferring heat from those outer portions of the contact tubes it contacts in the particular zone. The first stage reactor heat transfer zone is maintained at a temperature of 250° C. to 450° C., preferably 280° C. to 380° C.; and the second stage reactor heat transfer zone is maintained at a temperature of 220° C. to 450° C., preferably 240° C. to 360° C. The peak catalyst temperatures are 20° C. to 70° C. above the heat transfer medium temperature and are very sensitive to changes in the heat transfer medium temperature. Generally, increasing the heat transfer medium temperature by 1° C. will increase the peak catalyst temperature by 2–30° C. As is known in the art the catalyst will lose activity as it grows older. To compensate, reaction temperature must be increased to maintain production of acrolein and acrylic acid at desired levels.

The heat transfer medium may circulate within the reactor cocurrent or countercurrent with the flow of the reactant gasses through the reactor. It is preferred that the heat transfer medium circulates within the reactor countercurrent with the flow of the reactant gasses through the reactor. U.S. Pat. Nos. 4,256,783; 5,151,605; 5,739,391; and DE 2,201,528, describe and disclose contact tube and baffle arrangements in contact tube fixed bed shell reactors which provide for cocurrent, countercurrent, transverse and bypass flows of the heat transfer medium, such references being incorporated herein by reference for their teaching of heat transfer medium flow and reactor arrangements to accomplish the same. Furthermore, it is understood that the baffles may be arranged so as to have equal spacing between baffles or variable spacing between baffles.

The heat transfer medium may be any heat transfer medium suitable for use under the temperature conditions of the present invention. Generally the heat transfer medium is a salt melt, preferably a salt melt of 40 to 80, preferably 50 to 70 percent by weight potassium nitrate and 60 to 20, preferably 50 to 30 percent by weight sodium nitrite. In an alternative embodiment, the salt melt may include sodium nitrate as a substitute for sodium nitrite or potassium nitrate or sodium nitrate may be an additional component of the salt melt. The sodium nitrate, if used, is generally present at up to 20, preferably up to 10 percent by weight of the total salt composition. Other examples of heat transfer mediums include heat transfer oils, both oleaginous and synthetic, heat transfer fluids such as phenyl ethers and polyphenyls, and low melting metals such as sodium, tin, mercury, as well as low melting alloys of various metals.

As mentioned above, after being formed, the acrylic acid is absorbed in a tower to form an aqueous acrylic acid stream. The absorption may take place by methods known in the art, such as feeding the mixed product gas comprising acrylic acid up into an absorption tower and feeding water, recycled waste water, stripped waste water, or mixtures thereof down the tower, ensuring that there is good contact between the mixed product gas comprising acrylic acid and the water/liquid traveling down the tower. The mixed product gas comprising acrylic acid generally is fed to the absorption tower at from 200° C. to 400° C. Preferably, the mixed product gas comprising acrylic acid is fed to the absorption tower at from 250° C. to 350° C. The temperature in the absorption tower generally ranges from 30° C. to 100° C. Preferably, the temperature in the absorption tower ranges from 40° C. to 80° C. The water fed to the absorption tower may be city water, deionized water, recycled water from the process or other processes, or combinations thereof. The ratio of water fed to the absorption tower to the reactor propylene feed rate ranges from 0.35 to 1 to 1.5 to 1. Preferably, the ratio of water fed to the absorption tower to propylene feed rate ranges from 0.35 to 1.

Inhibitors are necessary to prevent polymerization during the absorption process. Suitable inhibitors include hydroquinone; 4-methoxyphenol; 4-ethoxyphenol; 4-propoxyphenol; 4-butoxyphenol; 4-heptoxyphenol; hydroquinone monobenzylether; 1.2-dihydroxybenzene; 2-methoxyphenol; 2,5-dichlorhydroquinone; 2,5-di-tert-butylhydroquinone; 2-acetylhydroquinone; hydroquinone monobenzoate; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino 2,2,6,6-tetramethyl-piperidinyloxy; 4-amino-2,2,6,6-tetramethyl-piperidinyloxy; 4-ethanoyloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy and mixtures thereof. The inhibitors typically are used at from 100 ppm to 1,000 ppm based on the total weight of water and monomer. The inhibitors may be added to the water being fed to the absorption tower or may be added through a separate inhibitor feed. In a preferred embodiment, the inhibitor is from 300 ppm to 700 ppm hydroquinone and is fed as part of the aqueous feed at the top of the absorption tower.

When formed by a low propylene feed process, the acrylic acid concentration in the aqueous acrylic acid stream typically ranges from 20% to 32% by weight. When formed by the high propylene feed process of this invention, the acrylic acid concentration in the aqueous acrylic acid stream may range from 32% to 55% by weight. This is called a concentrated aqueous acrylic acid stream. The high propylene feed process is more efficient because more acrylic acid is produced in the same or smaller equipment. The process is also more efficient because less steam feed is required, therefore there is less water in the aqueous stream, resulting in less waste water.

In an alternative embodiment, the concentrated aqueous acrylic acid stream may be obtained from different oxidation processes, such as a single reactor process.

In one embodiment, the concentrated aqueous acrylic acid stream is purified. Generally, the concentrated aqueous acrylic acid stream exits the bottom of absorber 4 and is fed to light ends stripper 5, where light ends including acrolein, propionaldehyde, acetaldehyde, formaldehyde, isopropyl acetate and the like are removed. The purified concentrated aqueous acrylic acid stream then enters a separation and purification process.

The purified concentrated aqueous acrylic acid stream exits the light ends stripper 5 and is fed to Podbielniak extractors 6 and a Karr column 7, where the acrylic acid is extracted into organic solvent to form an organic acrylic acid extract stream. As a result of the extraction, a raffinate stream is also formed.

The organic acrylic acid extract stream is then fed to an extract stripper 8, where water and the organic solvent are removed overhead, and an extract stripper stream containing mostly acrylic acid and acetic acid is removed from the bottom.

The water and organic solvent may be separated into an aqueous distillate stream and an organic distillate stream of toluene/isopropyl acetate. The organic distillate stream may be recycled. The aqueous distillate stream and the raffinate stream may be fed to a raffinate stripper 9, where they are distilled to generate a waste water stream and a recycle stream of toluene/isopropyl acetate.

The extract stripper stream is then sent to a crude column 10, where acetic acid is distilled out the top of the column, and a crude acrylic acid stream is removed from the bottom of the column.

The acetic acid from the top of the crude column 10, may be sent to an acetic acid distillation column 11, with acrylic acid going from the bottom of the column back to the crude acrylic acid column, and acetic acid exiting out the top of the column.

DESCRIPTION OF THE FIGURE

A detailed description of the purification process will now be provided. The acrylic acid in the aqueous acrylic acid stream must be purified. A first purification may take place through the use of a light ends stripper, 5. The light ends stripper may be a distillation column. The light ends stripper is used to remove acrolein, propionaldehyde, acetaldehyde, formaldehyde, isopropyl acetate and the like from the aqueous acrylic acid stream. The stripping gas or vapor may be generated from the contents of the reboiler or may be steam, air, absorber off gas, or gas from an incinerator stack. Alternatively, the bottoms of the light ends stripper may be reboiled or air may be utilized to strip the light ends from the aqueous acrylic acid. The light ends stripper is typically operated at a temperature of from 80° C. to 100° C. and a pressure of 100–200 mm Hg, preferably 160–200 mm Hg. The acrolein and other light ends removed from the top of the light ends stripper may be recycled to reactor 3, to improve the overall yield of the process.

The aqueous acrylic acid may be treated with a basic compound such as, but not limited to sodium hydroxide, potassium hydroxide, or calcium carbonate to react out maleic acid impurities. The basic compound is added at a stoichiometric ratio to the maleic acid impurity. Other additives such as oxazolidine derivatives may be added to the aqueous acrylic acid to reduce the level of aldehydes present in the crude acrylic acid product.

The aqueous acrylic acid stream requires further purification after the light ends stripper. This is accomplished through a separation scheme. The first step of the separation scheme may be the extraction of acrylic acid from the aqueous stream into an organic stream. This may be accomplished through the use of any extraction equipment known in the art, including, but not limited to Podbielniak extractors 6, Karr columns 7, or combinations thereof. The extractors may utilize gravity or centrifugal force to separate the acrylic acid from the aqueous stream into the organic stream. The aqueous acrylic acid stream may be fed to the extractors. An organic stream made from an organic solvent or a mixture of organic solvents is fed to the extractors countercurrent to the aqueous feed. Within the extractors intimate mixing occurs between the aqueous acrylic acid stream and the organic stream, resulting in the majority of the acrylic acid being extracted into the organic stream. The extraction process may be operated at a temperature ranging from 10° C. to 75° C. The mass basis ratio of the feed rate of the aqueous acrylic acid stream to the organic stream is typically from 3:1 to 0.8:1. Preferably, the mass basis ratio of the feed rate of the aqueous acrylic acid stream to the organic stream is typically from 1.5:1 to 0.8:1. The ratio of organic solvent to acrylic acid preferably ranges from 2.9:1 to 3.3:1.

Suitable organic solvents for the extraction of acrylic acid from the aqueous acrylic acid stream include isobutyl acetate, n-propyl acetate, methyl propyl ketone, methyl isobutyl ketone, heptane, toluene, isopropyl acetate, and mixtures thereof. A mixture of toluene and isopropyl acetate is preferred.

Where a mixture of toluene and isopropyl acetate is utilized, the ratio of toluene to isopropyl acetate may range from 1:1 to 1:4. Preferably, the ratio of toluene to isopropyl acetate ranges from 1:2 to 1:3. The extraction process provides two streams. One stream is termed the extract stream and contains mostly acrylic acid and organic solvent, with minor amounts of acetic acid and water. The other stream is termed the raffinate stream, which contains mostly water, acetic acid, and a minor amount of organic solvent.

The acrylic acid in the acrylic acid extract stream may be further purified by feeding the acrylic acid extract stream to an extract stripper 8. The extract stripper may be a distillation column. The distillation column may be equipped with sieve trays. The extract stripper may be used to perform an azeotropic distillation of the acrylic acid extract stream, resulting in water and toluene/isopropyl acetate being removed overhead, and an extract stripper stream containing mostly acrylic acid and acetic acid being removed from the bottom. The extract stripper is typically operated at a temperature of from 60° C. to 110° C., and a pressure of from 25 mm Hg to 75 mm Hg. Preferably, the extract stripper is operated at a temperature of from 80° C. to 95° C., and a pressure of from 40 mm Hg to 60 mm Hg.

Additional inhibitors are necessary to prevent polymerization in the extract stripper. Because the extract stripper may have sieve trays, a vapor phase inhibitor such as n-phenyl hydroxylamine or derivatives thereof may be useful. Liquid phase inhibitors such as those described for the absorption tower water may also be useful. Additionally, phenothiazine ("PTZ") may be useful to prevent polymerization in the liquid phase. The amount of inhibitor useful ranges from 0.1 ppm to 50 ppm for the vapor phase inhibitor, and from 1000 ppm to 5000 ppm for the liquid phase inhibitor.

In a preferred embodiment, the vapor phase inhibitor is added to the reboiler and the bottom trays of the column, while the liquid phase inhibitor is added to the top of the column.

The water and toluene/isopropyl acetate removed from the top of the extract stripper may be separated into an aqueous distillate stream and an organic distillate stream of toluene/isopropyl acetate. The toluene/isopropyl acetate stream may be recycled to the extract stripper to aid in the azeotropic distillation and to the extractors, while the aqueous stream may be recycled to a raffinate stripper 9.

The raffinate stripper 9 may be a distillation column. The raffinate stripper receives the raffinate stream from the extraction process and the aqueous stream from the extract stripper and separates the organic solvent contained in these streams through distillation. The stripping gas may be generated by the contents of the reboiler or may be steam. The raffinate stripper typically operates at a temperature of from 80° C. to 120° C. and atmospheric pressure. Preferably, the raffinate stripper operates at a temperature of from 95° C. to 110° C. This results in a stream of waste water and a recycle stream of toluene/isopropyl acetate. The waste water stream may be used as a water feed back to the absorber, or to dilute the aqueous acrylic acid feed stream, or may be disposed of in a waste water treatment plant. The toluene/isopropyl acetate may be used to generate new inhibitor feed streams or be recycled to the extraction step or the extract stripper.

The extract stripper stream containing mostly acrylic acid may be further purified by feeding the stream to at least one crude acrylic acid distillation column 10 and distilling an acetic acid rich stream out the top of the column, while removing a crude acrylic acid stream from the bottom of the column. By crude acrylic acid is meant a composition containing approximately 97% acrylic acid and at least one of the following impurities, acetic acid, propionic acid, β-acroloxypropionic acid, water, furfural, benzaldehyde, maleic acid, maleic anhydride, and protoanemonin. The crude acrylic acid column is typically operated at a temperature of from 70° C. to 110° C. and a pressure of from 30 mm Hg to 60 mm Hg. Preferably, the crude acrylic acid column is operated at a temperature of from 80° C. to 100° C. and a pressure of from 40 mm Hg to 50 mm Hg. When a second crude acrylic acid column is utilized, it may be operated at the same conditions as the first crude acrylic acid column.

The acetic acid rich stream from the top of the crude acrylic acid column may be fed to an acetic acid distillation column 11, with acrylic acid going from the bottom of the column back to the crude acrylic acid column, and acetic acid coming out the top of the column. The acetic acid column is typically operated at a temperature of from 80° C. to 120° C. and pressure of 30 mm Hg to 60 mm Hg. Preferably, the acetic acid column is operated at a temperature of from 85° C. to 105° C. and a pressure of from 40 mm Hg to 50 mm Hg. Optionally, a second crude acrylic acid column and an acetic acid column are included in the separation scheme.

Additional inhibitors may be necessary to prevent polymerization in at least one crude acrylic acid column and in the acetic acid column. As discussed above, suitable inhibitors include liquid phase inhibitors such as those useful in the absorption tower water, and n-phenyl hydroxylamine as a vapor phase inhibitor. The amounts of n-phenyl hydroxylamine inhibitor described above is applicable here. The n-phenyl hydroxylamine may be added at the bottom of the at least one crude acrylic acid column as well as the bottom of the acetic acid column. The amount of liquid phase inhibitor may range from 1 ppm to 1000 ppm, depending on the acrylic acid feed rate to the column. The liquid phase inhibitor may be added at the top of the at least one crude acrylic acid column as well as at the top of the acetic acid column.

Throughout this specification and claims, unless otherwise indicated, references to percentages are by molar volume and all temperatures are in degree centigrade.

It is also to be understood that for purposes of this specification and claims that the range and ratio limits, recited herein, are combinable. For example, if ranges of 1–20 and 5–15 are recited for a particular parameter, it is understood that ranges of 1–15 or 5–20 are also contemplated.

Throughout this specification and claims the terms "water vapor" and "steam" are understood to be synonymous.

Also, the term "major amount" is understood to mean greater than 50 percent by volume of the total composition. The term "minor amount" is understood to mean less than 50 percent by volume of the total composition.

The term "cocurrent" as used herein is meant to indicate that the current of separate, distinct flowing materials is proceeding in substantially the same general direction, regardless of any alterations such as meandering, transverse, or radial flow.

The term "countercurrent" as used herein is meant to indicate that the current of separate, distinct flowing materials is proceeding in substantially the opposite general direction, regardless of any alterations such as meandering, transverse, or radial flow.

The term "inert" as used herein is meant to indicate that the particular material does not participate in, is unaffected by, and/or is otherwise inactive in the acrylic acid reaction system disclosed herein. Accordingly, a material such as propane is easily reacted or combusted in other systems, but in the reaction system of the present invention is considered inert.

The conversion % of propylene=(#moles propylene converted/#of moles propylene employed)×100.

The selectivity % of acrylic acid=(#of moles of acrylic acid produced/#of moles propylene reacted)×100.

The yield of acrylic acid=(#of moles acrylic acid produced/#of moles propylene employed)×100.

The yield of acrolein=(#of moles acrolein produced/#of moles propylene employed)×100.

The following Examples are provided as an illustration of the present invention.

EXAMPLE 1

A feed composition containing 7.02% by volume chemical grade propylene, an amount of air and steam sufficient to maintain an oxygen/propylene ratio of 1.84 and 30.8% by volume water vapor were fed to the contact tubes of a shell and tube reactor. The reactants were introduced into the first stage contact tubes which were packed with ACF-2 catalyst, available from Nippon Shokubai K. K. of Osaka, Japan, and the mixed product gas including acrolein was passed through a salt cooled heat exchanger. The cooled mixed product gas was fed to the second stage contact tubes which were packed with ACS-6 catalyst also available from Nippon Shokubai K. K. The acrolein formation reaction in stage one was carried out at a salt temperature maintained at 320 to 330° C. and the acrylic acid formation reaction in stage two was carried out at a salt temperature maintained at 280 to 290° C. for a trial time of 14977 hours. The product gasses containing acrylic acid were introduced into an absorption tower to obtain an aqueous acrylic acid product solution having an average concentration of 31.7 weight %.

This Example shows the concentration of acrylic acid in the aqueous acrylic acid stream with a propylene feed of 7.02%.

EXAMPLE 2

A feed composition containing 7.89% by volume chemical grade propylene, an amount of air and steam sufficient to maintain an oxygen/propylene ratio of 1.86 and 21.5% by volume water vapor were fed to the contact tubes of a shell and tube reactor. The reactants were introduced into the contact tubes which were packed with ACF-2 catalyst and ACS-6 catalyst as described in Example 1. The acrolein formation reaction in stage one was carried out at a salt temperature maintained at 320 to 330° C. and the acrylic acid formation reaction in stage two was carried out at a salt temperature maintained at 280 to 290° C. for a trial time of 16285 hours. The product gasses containing acrylic acid were introduced into an absorption tower to obtain an aqueous acrylic acid product solution having an average concentration of 40.7 weight %.

This Example shows that an increase in the feed of propylene from 7.02% to 7.89% increased the concentration of acrylic acid in the aqueous acrylic acid stream from 31.7% to 40.7%. This is important because the slight increase in propylene feed enables a large reduction in waste water generated by the process.

EXAMPLE 3

The purification process of this invention centers around the separation of acrylic acid from acetic acid and water utilizing liquid-liquid extraction and azeotropic distillation. The efficiency of the process is measured by the acrylic acid recovery in the crude acrylic acid column bottoms stream. The losses of acrylic acid occur in the raffinate stream from the extraction and in the aqueous distillate from the azeotropic distillation column.

An aqueous mixture containing 37.7 weight percent acrylic acid, 2.2 weight percent acetic acid, and 60 weight percent water was contacted with a recycle solvent mixture containing 70.7 weight percent isopropyl acetate, 28.8 weight percent toluene, 0.2 weight percent acetic acid and 0.3 weight percent water in the liquid-liquid extractors as described by FIG. 1. The resulting extract stream contained 20.99 weight percent acrylic acid and the raffinate stream contained 0.40 weight percent acrylic acid. The single pass yield for the extraction was 95.96%.

The extract mixture was fed to an azeotropic distillation column to remove water, isopropyl acetate, and toluene from the extract stream as illustrated in FIG. 1. The extract stripper bottoms contained 96.38 weight percent acrylic acid, 3.09 weight percent acetic acid, 0.01 weight percent water, 908 ppm isopropyl acetate, and 98 ppm toluene. The extract stripper bottoms stream was introduced into two crude acrylic acid distillation columns as described in FIG. 1, and the bottoms product from these columns contained an average concentration of 96.8 weight percent acrylic acid. The distillate streams of the crude acrylic acid columns were fed to an acetic acid removal column and the distillate stream contained an average concentration of 90.84 weight percent acetic acid as illustrated in FIG. 1.

Results

The overall yield, as defined by the ratio of the acrylic acid in the crude column bottoms to acrylic acid in the feed to the extraction was 94.4% for this example. This Example shows that the purification process works well with an initial acrylic acid concentration of 37.7% in the aqueous acrylic acid stream.

EXAMPLE 4

An aqueous mixture containing 44.66 weight percent acrylic acid, 2.67 weight percent acetic acid, and 52.66 weight percent water was contacted with a recycle solvent mixture containing 70.17 weight percent isopropyl acetate, 28.83 weight percent toluene, 0.39 weight percent acetic acid and 0.31 weight percent water in the liquid-liquid extractors as described by FIG. 1. The resulting extract stream contained 23.20 weight percent acrylic acid and the raffinate stream contained 0.45 weight percent acrylic acid. The single pass yield for the extraction was 96.0%.

The extract mixture was fed to an azeotropic distillation column to remove water, isopropyl acetate, and toluene from the extract stream as illustrated in FIG. 1. The extract stripper bottoms contained 95.42 weight percent acrylic acid, 2.96 weight percent acetic acid, 0.03 weight percent water, 1122 ppm isopropyl acetate, and 65 ppm toluene. The extract stripper bottoms stream was introduced into two crude acrylic acid distillation columns as described in FIG. 1, and the bottoms product from these columns contained an average concentration of 96.6 weight percent acrylic acid. The distillate streams of the crude acrylic acid columns were fed to an acetic acid removal column and the distillate stream contained an average concentration of 90.41 weight percent acetic acid as illustrated in FIG. 1.

Results

The overall yield, as defined by the ratio of the acrylic acid in the crude column bottoms to acrylic acid in the feed to the extraction was 95.3% for this example. This Example shows that the purification process of this invention enables increased throughput without sacrificing efficiency. The acrylic acid concentration in the aqueous acrylic acid was increased from 37.7% to 44.7%, yet the purification process resulted in the same single pass yield for the extraction, and the overall yield was not sacrificed.

EXAMPLE 5

Increased Organic Stream to Aqueous Acrylic Acid Stream Ratio

An aqueous mixture containing 42.40 weight percent acrylic acid, 2.20 weight percent acetic acid, and 53.40 weight percent water was contacted with a recycle solvent mixture containing 69.66 weight percent isopropyl acetate, 28.68 weight percent toluene, 0.40 weight percent acetic acid, 0.11 weight percent acrylic acid and 1.12 weight percent water in the liquid-liquid extractors as described by FIG. 1. The resulting extraction was carried out at a solvent to acrylic acid mass ratio of 3.05. The extract stream contained 21.45 weight percent acrylic acid, 1.26 weight percent acetic acid, 6.55 weight percent water, 46.03 weight percent isopropyl acetate and 18.95 weight percent toluene. The raffinate stream contained 0.07 weight percent acrylic acid, 0.45 weight percent acetic acid and 92.92 weight percent water. The temperature of the extract stream was 17° C. and the temperature of the raffinate was 28° C. The single pass efficiency for the recovery of acrylic acid in the extraction was 98.7%.

The extract mixture was fed to an azeotropic distillation column to remove water, isopropyl acetate, and toluene from the extract stream as illustrated in FIG. 1. The extract stripper bottoms contained 96.74 weight percent acrylic acid, 2.36 weight percent acetic acid, 0.83 weight percent acrylic acid dimer, 0.01 weight percent water, 0.024 weight percent isopropyl acetate, and 40 ppm toluene. The separation was performed at 50 millimeters mercury absolute pressure and a bottoms temperature of 86° C.

The distillate stream from the extract stripper was separated into two phases in a gravity separator at 8° C. The organic phase was recycled to the extraction and the aqueous phase was sent to the raffinate stripper column for isopropyl acetate and toluene recovery. The raffinate stripper operated with an average packing temperature of 99.6° C. and at a pressure of 760 millimeters absolute.

The extract stripper bottoms stream was introduced into two crude acrylic acid distillation columns as described in FIG. 1, and the bottoms product from these columns contained an average concentration of 97.95 weight percent acrylic acid, 0.037 weight percent acetic acid, 1.97 weight percent acrylic acid dimer. The separation was performed at 45 millimeters mercury absolute pressure and a bottoms temperature of 85° C.

The distillate streams of the crude acrylic acid columns were fed to an acetic acid removal column and the distillate stream contained an average concentration of 92.21 weight percent acetic acid, 3.11 weight percent acrylic acid, 4.06 weight percent water 0.69 weight percent isopropyl acetate and 0.09 weight percent toluene as illustrated in FIG. 1. The separation was performed at 45 millimeters mercury pressure absolute and a bottoms temperature of 90° C.

The bottom stream from the acetic acid removal column was returned to the crude columns to provide interchange for additional purification. The overall efficiency of the process, as defined by the ratio of the acrylic acid in the crude column bottoms to acrylic acid in the feed to the extraction was 96.2% for this example.

Results

This Example shows the effect of changing the ratio of the organic stream to the aqueous acrylic acid stream during the extraction step. The single pass efficiency for the recovery of acrylic acid in the extraction was 98.7%, a 2.2% improvement over the comparative Example below.

EXAMPLE 6 (Comparative)

An aqueous mixture containing 42.85 weight percent acrylic acid, 2.57 weight percent acetic acid, and 52.58 weight percent water was contacted with a recycle solvent mixture containing 68.46 weight percent isopropyl acetate, 29.67 weight percent toluene, 0.96 weight percent acetic acid, 0.41 weight percent acrylic acid and 0.33 weight percent water in the liquid-liquid extractors as described by FIG. 1. The resulting extraction was carried out at a solvent to acrylic acid ratio of 2.67. The extract stream contained 25.41 weight percent acrylic acid, 1.54 weight percent acetic acid, 7.62 weight percent water, 46.27 weight percent isopropyl acetate and 20.30 weight percent toluene. The raffinate stream contained 0.59 weight percent acrylic acid, 1.18 weight percent acetic acid, 2.59 weight percent isopropyl acetate, 0.04 weight percent toluene and 93.88 weight percent water. The temperature of the extract stream was 14° C. and the temperature of the raffinate was 28° C. The single pass efficiency for acrylic acid recovery in the extraction was 96.5%.

The extract mixture was fed to an azeotropic distillation column to remove water, isopropyl acetate, and toluene from the extract stream as illustrated in FIG. 1. The extract stripper bottoms contained 95.37 weight percent acrylic acid, 3.62 weight percent acetic acid, 0.96 weight percent acrylic acid dimer, 0.01 weight percent water, 290 ppm isopropyl acetate, and 20 ppm toluene. The separation was performed at 50 millimeters mercury pressure absolute and a bottoms temperature of 88° C.

The distillate stream from the extract stripper was separated into two phases in a gravity separator at 8° C. The organic phase was recycled to the extraction and the aqueous phase was sent to the raffinate stripper column for isopropyl acetate and toluene recovery. The raffinate stripper operated with an average packing temperature of 99.7° C. and at a pressure of 760 millimeters absolute.

The extract stripper bottoms stream was introduced into two crude acrylic acid distillation columns as described in FIG. 1, and the bottoms product from these columns contained an average concentration of 96.82 weight percent acrylic acid, 0.097 weight percent acetic acid, 2.23 weight percent acrylic acid dimer. The separation was performed at 45 millimeters mercury absolute pressure and a bottoms temperature of 85° C.

The distillate streams of the crude acrylic acid columns were fed to an acetic acid removal column and the distillate stream contained an average concentration of 95.01 weight percent acetic acid, 3.51 weight percent acrylic acid, 1.48 weight percent isopropyl acetate as illustrated in FIG. 1. The separation was performed at 45 millimeters Mercury pressure absolute and a bottoms temperature of 90° C. The bottom stream from the acetic acid removal column was returned to the crude columns to provide interchange for additional purification. The overall efficiency of the process, as defined by the ratio of the acrylic acid in the crude column bottoms to acrylic acid in the feed to the extraction was 94.6% for this example.

We claim:
1. A process comprising the steps of:
(A) feeding a reactant composition comprising: (i) greater that 7 percent by volume propylene, (ii) oxygen, (iii) water vapor, and (iv) the remainder including a major amount of at least one inert gas, into a reactor; the reactor including a plurality of contact tubes, containing at least one catalyst, disposed in a shell, wherein the inside of the reactor shell contains at least one heat transfer zone through which heat transfer medium passes and each contact tube comprises at least one reaction zone capable of effecting the preparation of acrolein from propylene,
(B) contacting the reactant composition with the at least one reaction zone to form a mixed product gas comprising actolein,
(C) cooling the mixed product gas comprising acrolein in a heat exchanger,
(D) feeding the cooled mixed product gas comprising acrolein to a second reactor; the second reactor including a plurality of contact tubes, containing at least one catalyst, disposed in a shell, wherein the inside of the reactor shell contains at least one heat transfer zone through which a heat transfer medium passes and each contact tube comprises at least one reaction zone capable of effecting the preparation of acrylic acid from acrolein, and (E) contacting the mixed product gas comprising acrolein with the at least one reaction zone to form a mixed product gas comprising acrylic acid;

wherein the mixed product gas comprising acrylic acid is absorbed in an absorption tower with water and at least one polymerization inhibitor to form an aqueous acrylic acid stream containing from 32% to 55% by weight acrylic acid; said process further comprising purifying the acrylic acid wherein the purification comprises:

feeding the aqueous acrylic acid stream to a fight ends stripper to remove light ends from the aqueous acrylic acid stream, contacting the aqueous acrylic acid stream from the light ends stripper with an organic stream selected from toluene, isopropyl acetate and combinations thereof in at least one extractor to generate an extract stream and a raffinate stream, feeding the extract stream to an extract stripper comprising a reboiler and a column having a top and lower trays, wherein a vapor phase polymerization inhibitor is added to the reboiler and lower trays of the column, and a liquid phase polymerization inhibitor is added to the top of the column, and wherein a water and toluene/isopropyl acetate stream and an extract stripper stream are generated, feeding the raffinate stream to a raffinate stripper to generate a waste water stream and a toluene/isopropyl acetate recycle stream, feeding the extract stripper stream to at least one crude acrylic acid distillation column to generate an acetic acid stream from the top of the column and a crude acrylic acid stream, separating the water and toluene/isopropyl acetate stream into a toluene/isopropyl acetate steam, which optionally is recycled to the extract stripper, and an aqueous steam, which optionally is recycled to the raffinate stripper.

2. The process according to claim 1, wherein the ratio of the organic stream to the aqueous acrylic acid stream is from 2.9 to 1 to 3.3 to 1.

3. The process according to claim 1, wherein the purification further comprises: feeding the acetic acid stream to an acetic acid distillation column to generate acetic acid from the top of the column and return acrylic acid from the bottom of the column to the crude acrylic acid column, and feeding the wastewater to absorbers in different acrylic acid production units.

4. A process for purifying a concentrated aqueous acrylic acid stream comprising:

feeding the concentrated aqueous acrylic acid stream to a light ends stripper to remove light ends from the concentrated aqueous acrylic acid stream contacting the aqueous acrylic acid stream from the light ends stripper with an organic stream selected from toluene, isopropyl acetate and combinations thereof in at least one extractor to generate an extract stream and a raffinate stream, feeding the extract stream to an extract stripper comprising a reboiler and a column having a top and lower trays, wherein a vapor phase polymerization inhibitor is added to the reboiler and lower trays of the column, and a liquid phase polymerization inhibitor is added to the top of the column, and wherein a water and toluene/isopropyl acetate stream and an extract tripper stream are generated, feeding the raffinate stream to a raffinate stripper to generate a waste water stream and a toluene/isopropyl acetate recycle stream, feeding the extract stripper stream to at least one crude acrylic acid distillation column to generate an acetic acid stream from the top of the column and a crude acrylic acid stream, separating the water and toluene/isopropyl acetate stream into a toluene/isopropyl acetate stream, which optionally is recycled to the extract stripper, and an aqueous stream, which optionally is recycled to the raffinate stripper.

5. The process according to claim 4, wherein the ratio of the porganic stream to the queous acrylic stream is from 2.9 to 1 to 3.3 to 1.

6. The process according to claim 4, wherein the purification further comprises: feeding the acetic acid stream to n acetic acid distillation column to generate acetic acid from the top of the column and return acrylic acid from the bottom of the column to the crude acrylic acid column, and feeding the wastewater to absorbers in different acrylic acid production units.

7. The process according to claim 6, wherein the purification further comprises: forming a mixture by adding a compound selected from the group consisting of aniline, isomers of toluidine, isomers of phenylenediamine, hydrazine and its derivatives, or combinations thereof to the crude acrylic acid, distilling the mixture, and taking pure acrylic acid out the bottom of the column.

8. The process according to claim 1, wherein the heat exchange medium passes through the heat transfer zone in the first reactor countercurrent to the reactant composition.

9. The process according to claim 1, wherein the heat exchange medium passes through the heat transfer zone in the first reactor cocurrent to the reactant composition.

10. The process according to claim 1, wherein the heat exchange medium passes through the heat transfer zone in the second reactor countercurrent to the reactant composition.

11. The process according to claim 1, wherein the heat exchange medium passes through the heat transfer zone in the second reactor cocurrent to the reactant composition.

* * * * *